US006841695B2

(12) United States Patent
Bollinger et al.

(10) Patent No.: US 6,841,695 B2
(45) Date of Patent: Jan. 11, 2005

(54) PROCESS FOR PREPARING DITHIOESTERS

(75) Inventors: Joseph Martin Bollinger, North Wales, PA (US); Jen-Lung Wang, Collegeville, PA (US)

(73) Assignee: Rohmax Additives GmbH, Darmstadt (DE)

( * ) Notice: Subject to any disclaimer, the term of this patent is extended or adjusted under 35 U.S.C. 154(b) by 0 days.

(21) Appl. No.: 10/390,015

(22) Filed: Mar. 18, 2003

(65) Prior Publication Data

US 2004/0186302 A1 Sep. 23, 2004

(51) Int. Cl.[7] .............................................. C07C 327/00
(52) U.S. Cl. ...................................... 558/230
(58) Field of Search ........................................ 558/230

(56) References Cited

U.S. PATENT DOCUMENTS 4,455,262 A   6/1984   Detienne et al.
6,458,968 B2  10/2002  Benicewicz et al.

FOREIGN PATENT DOCUMENTS

WO    WO 98/01478    1/1998

OTHER PUBLICATIONS

Houben–Weyl "Methoden der Organishen Chemie", vol. E5, pp. 891–916, 1985.
Hans de Brouwer–Experimental Procedures,"3.4.3 Synthesis of 2–phenylprop–2–yl Dithlobenzoate", pp. 79–86, 2001.

*Primary Examiner*—Rita Desai
*Assistant Examiner*—Robert Shiao
(74) *Attorney, Agent, or Firm*—Oblon, Spivak, McClelland, Maier & Neustadt, P.C.

(57) ABSTRACT

The present invention relates to a process for preparing dithioesters in which a dithiocarboxylic acid and/or a dithiocarboxylic salt is reacted with a vinyl compound and/or an alkyl compound which includes a leaving group, the reaction being carried out in a biphasic system in which one of the phases comprises water and the weight ratio of the aqueous phase to the organic phase lies in the range from 95:5 to 5:95.

22 Claims, No Drawings

PROCESS FOR PREPARING DITHIOESTERS

The present invention relates to a process for preparing dithioesters.

Processes for preparing dithiocarboxylic acids and dithiocarboxylic esters have been known for some time (cf. Houben-Weyl "Methoden der Organischen Chemie", Vol. E5, 1985, pages 891 to 916).

Owing to new developments in the field of free-radical polymerization, dithioesters are becoming increasingly important. RAFT (Reversible Addition Fragmentation Chain Transfer) is an important polymerization technique in order to prepare polymers having a narrow molecular weight distribution which are built up in a controlled way. It has been generally shown that dithioesters having a particular substitution pattern are particularly suitable for this purpose. For example, the patent U.S. Pat. No. 6,458,968 describes processes for preparing dithioesters which can be used for RAFT polymerization.

However, customary methods for preparing such compounds are associated with grave disadvantages. In some cases, relatively expensive compounds have to be used, or else the yield of the desired product is relatively low. Furthermore, many compounds which are used for preparing dithioesters are relatively sensitive toward oxygen or water.

A particular ester belonging to the preferred dithioesters which can be used for RAFT polymerization is cumyl dithiobenzoate (2-phenylprop-2-yl dithiobenzoate).

A synthetic route for preparing this compound comprises the addition of dithiobenzoic acid to α-methylstyrene.

Some authors have reported that the synthesis of dithioesters by this reaction route leads to a low yield of less than 35%, with preparative chromatography being required to isolate suitable compounds (cf. WO 98/01478 and Hans de Brouwer, Ph.D. Thesis, Technical University Eindhoven, 2001, "RAFT memorabilia: living radical polymerization in homogeneous and heterogeneous media"). The work of H. de Brouwer explains in particular that an increase of the yield using Brønsted and Lewis acids even under an inert gas atmosphere with careful handling of the dithiocarboxylic acid intermediate does not lead to an improvement in yield, as was shown in repeated experiments.

In view of the prior art identified and discussed herein, the object on which the present invention was based is to provide a process for preparing dithioesters which allows a particularly high yield.

In particular, it should be possible to carry out the process inexpensively. It was therefore a further object of the invention to provide a process for preparing dithioesters which should be implementable in a simple manner on the industrial scale. In this connection, it should in particular be possible to use existing plants.

Furthermore, it was therefore an object of the present invention to provide a process for preparing dithiocarboxylic esters in which the process products obtained can be used in RAFT polymerizations without complicated purification methods, in particular without chromatographic processes.

These and further objects which are not specified in detail but are immediately obvious to those skilled in the art from the introductory discussions of the prior art are achieved according to the invention by a process having the features of claim 1. Advantageous modifications of the process according to the invention are protected in the claims relating back to claim 1.

The performance of the reaction in a biphasic system, one of the phases comprising water and the weight ratio of the aqueous phase to the organic phase lying in the range from 95:5 to 5:95, surprisingly provides a process for preparing dithiocarboxylic esters in which a dithiocarboxylic acid and/or a dithiocarboxylic salt is reacted with a vinyl compound and/or an alkyl compound having a leaving group, in which very high yields can be achieved.

Furthermore, the process according to the invention achieves a series of advantages over the prior art which were not immediately foreseeable. These include, among others:

The process can easily be carried out in existing plants.

The process can be carried out using relatively inexpensive chemicals.

Furthermore, the process according to the invention allows the preparation of dithioesters on the industrial scale.

Moreover, the dithiocarboxylic esters prepared by the process according to the invention can be used in RAFT polymerizations without complicated purification, dispensing in particular with chromatographic processes.

In the process of the present invention, dithiocarboxylic acids and/or dithiocarboxylic salts are used. These compounds are known to those skilled in the art, and their preparation is described, for example, in Houben-Weyl, Methoden der Organischen Chemie Vol. E5, 1985, pp. 891 to 916, and also in U.S. Pat. No. 4,455,262.

For example, dithiocarboxylic acids or their salts can be obtained by reacting an organometallic compound with carbon disulfide.

The dithiocarboxylic acid compound includes a free-radical-stabilizing substituent, preferably in the α-position to the dithiocarboxylic acid group. These substituents include, among others, -aryl, heteraryl, —CN, —COR and —$CO_2R$, where R is in each case an alkyl or aryl radical, aromatic and/or heteroaromatic groups, although preference is given to aromatic groups.

According to the invention, aromatic groups refer to radicals of mono- or polycyclic aromatic compounds having preferably from 6 to 20, in particular from 6 to 12 carbon atoms. Heteroaromatic groups indicate aryl radicals in which at least one CH group is replaced by N and/or at least two neighboring CH groups are replaced by S, NH or O, and heteroaromatic groups may have from 3 to 19 carbon atoms.

Aromatic or heteroaromatic groups which are preferred according to the invention are derived from benzene, naphthalene, biphenyl, diphenyl ether, diphenylmethane, diphenyldimethylmethane, bisphenone, diphenyl sulfone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, bipyridine, pyrazine, pyrazole, pyrimidine, pyridazine, 1,3,5-triazine, 1,2,4-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzooxathiadiazole, benzooxadiazole, benzopyridine, benzopyrazine, benzopyrazidine, benzopyrimidine, benzotriazine, indolizine, pyridopyridine, imidazopyrimidine, pyrazinopyrimidine, carbazole, acridine, phenazine, benzoquinoline, phenoxazine, phenothiazine, acridizine, benzopteridine, phenanthroline and phenanthrene, each of which may optionally also be substituted.

In a particular aspect of the present invention, the dithiocarboxylic acid compound or its salt includes from 1 to 8, preferably from 1 to 6 and particularly preferably from 1 to 3, dithiocarboxylic acid groups. Useful salts are in particular alkali metal salts, for example sodium, potassium or lithium salts, ammonium salts and also alkaline earth metal salts, for example magnesium or calcium salts.

In a particular embodiment of the present process, a dithiocarboxylic acid or a dithiocarboxylic salt of the formula 1

(I)

is used where $R_1$ is a group having from 1 to 20 carbon atoms, m is an integer from 1 to 6 and M is a hydrogen atom, an alkali metal ion, an ammonium ion (primary, secondary, tertiary or quaternary ammonium ions may also be used) or a group including alkaline earth metal ions. When M is a group including alkaline earth metal ions, the second charge of the metal ion may be balanced, for example, by a halide ion, for example bromide or chloride, or a further dicarboxylic acid group, so that M may be, inter alia, MgBr, MgCl or $MgS_2CR_1$.

The expression "group having from 1 to 20 carbons" indicates radicals of organic compounds having from 1 to 20 carbon atoms. In addition to the aromatic and heteroaromatic groups already mentioned hereinabove, it encompasses, inter alia, alkyl, cycloalkyl, alkoxy, cycloalkoxy, alkenyl, alkanoyl, alkoxycarbonyl groups and also heteroaliphatic groups. The groups mentioned may be branched or unbranched. These groups may furthermore have customary substituents. Examples of substituents include linear and branched alkyl groups having from 1 to 6 carbon atoms, for example methyl, ethyl, propyl, butyl, pentyl, 2-methylbutyl or hexyl; cycloalkyl groups, for example cyclopentyl and cyclohexyl; aromatic groups such as phenyl or naphthyl; amino groups, ether groups, ester groups and also halides.

The preferred alkyl groups include methyl, ethyl, propyl, isopropyl, 1-butyl, 2-butyl, 2-methylpropyl, tert-butyl radicals, pentyl, 2-methylbutyl, 1,1-dimethylpropyl, hexyl, heptyl, octyl, 1,1,3,3-tetramethylbutyl, nonyl, 1-decyl, 2-decyl, undecyl, dodecyl, pentadecyl and the eicosyl groups.

The preferred cycloalkyl groups include the cyclopropyl, cyclobutyl, cyclopentyl, cyclohexyl, cycloheptyl and the cyclooctyl groups, each of which may optionally be substituted by branched or unbranched alkyl groups.

The preferred alkenyl groups include the vinyl, allyl, 2-methyl-2-propenyl, 2-butenyl, 2-pentenyl, 2-decenyl and the 2-eicosenyl groups.

The preferred alkynyl groups include the ethynyl, propargyl, 2-methyl-2-propynyl, 2-butynyl, 2-pentynyl and the 2-decynyl groups, The preferred alkanoyl groups include the formyl, acetyl, propionyl, 2-methylpropionyl, butyryl, valeroyl, pivaloyl, hexanoyl, decanoyl and the dodecanoyl groups.

The preferred alkoxycarbonyl groups include the methoxycarbonyl, ethoxycarbonyl, propoxycarbonyl, butoxycarbonyl, tert-butoxycarbonyl group, hexyloxycarbonyl, 2-methylhexyloxycarbonyl, decyloxycarbonyl or dodecyloxycarbonyl group.

The preferred alkoxy groups include alkoxy groups whose hydrocarbon radical is one of the aforementioned preferred alkyl groups.

The preferred cycloalkoxy groups include cycloalkoxy groups whose hydrocarbon radical is one of the aforementioned preferred cycloalkyl groups.

The preferred heteroaliphatic groups include the aforementioned preferred cycloalkyl radicals in which at least one carbon unit is replaced by O, S or an $NR^2$ group and $R^2$ is hydrogen, an alkyl group having from 1 to 6 carbon atoms, an alkoxy group having from 1 to 6 carbon atoms or an aryl group.

The preferred dithiocarboxylic acids include, inter alia, phenyldithiobenzoic acid, p-chlorodithiobenzoic acid, thiophene-2-dithiocarboxylic acid or furan-2-dithiocarboxylic acid, o-, m-, p-alkyldithiobenzoic acid, o-, m-, p-, halodithiobenzoic acids, polyalkyldithiobenzoic acids, and others similarly substituted aryl moieties. Preference is likewise given to the salts of these acids.

According to the invention, the dithiocarboxylic acid and/or a salt thereof is reacted with a vinyl compound and/or an alkyl compound which includes a leaving group. Such compounds are likewise known to those skilled in the art.

In a particular aspect of the present invention, the alkyl compound having a leaving group used is an alkyl halide, for example a chloride, an iodide or a bromide, an alkyl compound having a pseudohalide group, for example $N_3$ or SCN, or an alkyl compound having a sulfonate group, for example a triflate group.

Preference is given to reacting the dithiocarboxylic acid or salt thereof with a vinyl compound of the formula (II)

(II)

where the $R_2$, $R_3$, $R_4$ and $R_5$ radicals are each independently hydrogen or a radical having from 1 to 20 carbon atoms. Particular preference is given to at least one of the $R_2$, $R_3$, $R_4$ and/or $R_5$ radicals being an aromatic group.

The preferred vinyl compounds include, inter alia, styrene, substituted styrenes having one alkyl substituent in the side chain, for example α-methylstyrene and α-ethylstyrene, substituted styrenes having an alkyl substituent on the ring, such as vinyltoluene and p-methylstyrene, halogenated styrenes, for example monochlorostyrenes, dichlorostyrenes, tribromostyrenes and tetrabromostyrenes; heterocyclic vinyl compounds such as 2-vinylpyridine, 3-vinylpyridine, 2-methyl-5-vinylpyridine, 3-ethyl-4-vinylpyridine, 2,3-dimethyl-5-vinylpyridine, vinylpyrimidine, vinylpiperidine, 9-vinylcarbazole, 3-vinylcarbazole, 4-vinylcarbazole, 1-vinylimidazole, 2-methyl-1-vinylimidazole, N-vinylpyrrolidone, 2-vinylpyrrolidone, N-vinylpyrrolidine, 3-vinylpyrrolidine, N-vinylcaprolactam, N-vinylbutyrolactam, vinyloxolane, vinylfuran, vinylthiophene, vinylthiolane, vinylthiazoles and hydrogenated vinylthiazoles, vinyloxazoles and hydrogenated vinyloxazoles; vinyl and isoprenyl ethers.

In general, the alkyl compound having a leaving group may be described by the formula (III)

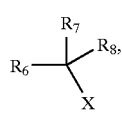

(III)

where the $R_6$, $R_7$ and $R_8$ radicals are each independently hydrogen or a radical having from 1 to 20 carbon atoms and X is a leaving group.

The leaving group X in formula (III) is preferably a halogen atom, for example chlorine, bromine or iodine, a pseudohalogen atom group, for example $N_3$ or SCN, or a group of the formula $O_3S$—$R_9$ where $R_9$ is a group comprising from 1 to 20 carbon atoms, for example a triflate group.

The preferred alkyl compounds having a leaving group include, inter alia, benzyl halides, such as p-chloromethylstyrene, α-dichloroxylene, α,α-dichloroxylene, α,α-dibromoxylene and hexakis(α-bromomethyl)benzene, benzyl chloride, benzyl bromide, 1-bromo-1-phenylethane, 1-chloro-1-phenylethane, cumyl chloride and cumyl bromide; carboxylic acid derivatives which are halogenated at the α-position, for example propyl-2-bromopropionate, methyl 2-chloropropionate, ethyl 2-chloropropionate, methyl 2-bromopropionate, ethyl 2-bromoisobutyrate; tosyl compounds such as benzyl tosylate and cumyl tosylate.

According to the invention, the process is carried out in a biphasic system, one of the phases comprising water and the weight ratio of the aqueous phase to the organic phase lying in the range from 95:5 to 5:95, preferably from 80:20 to 20:80.

The organic phase preferably comprises an inert organic solvent. For the purposes of the present invention, inert means that the solvent is not changed in the reaction of dithiocarboxylic salt with the vinyl and/or an alkyl compound having a leaving group. Examples of these solvents include aromatic hydrocarbons, esters, ethers and also aliphatic hydrocarbons. Among these, preference is given to aliphatic hydrocarbons. These aliphatic hydrocarbons include in particular hexane, heptane, octane and nonane, and higher homologs. Furthermore, the inert organic solvent used may be mineral oil or polyalpha olefins of various viscosities.

Mineral oils are known per se and commercially obtainable. They are generally obtained from petroleum or crude oil by distillation and/or refining and optionally further purification and finishing processes, the term mineral oil including in particular the higher-boiling fractions of crude oil or petroleum. In general, the boiling point of mineral oil is higher than 200° C., preferably higher than 300° C., at 5000 Pa. Preparation by low-temperature carbonization of shale oil, coking of hard coal, distillation of brown coal with the exclusion of air and also hydrogenation of hard coal or brown coal is likewise possible. A small proportion of mineral oils are also prepared from raw materials of plant (for example from jojoba, rape) or animal (for example neatsfoot oil) origin. Accordingly, mineral oils, depending on their origin, have different proportions of aromatic, cyclic, branched and linear hydrocarbons.

Polyalpha olefins are well-known and are commercially available with viscosities of 2, 4, 6, 100, cSt. at 100° C. They are generally produced by oligomerization of alpha olefins.

In general, a distinction is drawn between paraffin-based, naphthenic and aromatic fractions in crude oils or mineral oils, the terms paraffin-based fraction referring to relatively long-chain or highly branched isoalkanes and naphthenic fraction referring to cycloalkanes. Furthermore, depending on their origin and finishing, mineral oils have different proportions of n-alkanes, isoalkanes having a low degree of branching, known as monomethyl-branched paraffins, and compounds having heteroatoms, especially O, N and/or S, to which polar properties are imparted to a limited extent. However, classification is difficult, since individual alkane molecules may have both long-chain branched groups and cycloalkane radicals and aromatic fractions. For the purposes of the present invention, the classification may be effected, for example, according to DIN 51 378. Polar fractions may also be determined according to ASTM D 2007.

The proportion of n-alkanes in preferred mineral oils is less than 3% by weight, and the proportion of O, N and/or S-containing compounds less than 6% by weight. The proportion of aromatics and monomethyl-branched paraffins is generally in each case in the range from 0 to 40% by weight. In an interesting aspect, mineral oil comprises mainly naphthenic and paraffin-based alkanes which generally have more than 13, preferably more than 18 and very particularly preferably more than 20, carbon atoms. The proportion of these compounds is generally $\geq 60\%$ by weight, preferably $\geq 80\%$ by weight, although this is not intended to imply any restriction. A preferred mineral oil comprises from 0.5 to 30% by weight of aromatic fractions, from 15 to 40% by weight of naphthenic fractions, from 35 to 80% by weight of paraffin-based fraction, up to 3% by weight of n-alkanes and from 0.05 to 5% by weight of polar compounds, based in each case on the total weight of the mineral oil.

An analysis of particularly preferred mineral oils: which was effected by means of conventional processes such as urea separation and liquid chromatography on silica gel shows, for example, the following components, the percentages being based on the total weight of the mineral oil used in each case:

n-alkanes having from approx. 18 to 31 carbon atoms: 0.7–1.0%,
alkanes having little branching and from 18 to 31 carbon atoms:
1.0–8.0%,
aromatics having from 14 to 32 carbon atoms;
0.4–10.7%,
iso- and cycloalkanes having from 20 to 32 carbon atoms: 60.7–82.4%,
polar compounds:
0.1–0.8%,
loss:
6.9–19.4%.

Useful information with regard to the analysis of mineral oils and also a list of mineral oils which have a differing composition can be found, for example, in Ullmanns Encyclopedia of Industrial Chemistry, $5^{th}$ Edition on CD-ROM, 1997, keyword "lubricants and related products".

In a particular embodiment of the present process, a haloalkyl compound and/or a vinyl compound is dissolved in the organic phase.

When reacting vinyl compounds, free-radical inhibitors may be added to the organic phase. These include in particular sterically hindered phenols, sterically hindered amines and also catechols, tocopherols, gallate esters, and others known to be antioxidants.

In addition to water, the aqueous phase may comprise further components, for example water soluble organic compounds, for example alcohols or phase transfer catalysts, for example crown ethers or triicaprylmethylammonium chloride, and other variously substituted ammonium and phosphonium salts.

Preference is given to adjusting the pH of the aqueous phase to a value less than or equal to 6, preferably less than or equal to 4. In a particular aspect of the present invention, this is achieved by a strong acid, which generally has a $pK_a$ less than or equal to 4, in particular less than or equal to 2. The $pK_a$ is determined under standard conditions at a temperature of 20° C. These acids are known to those skilled in the art and include in particular hydrogen chloride, hydrogen bromide, hydrogen iodide, sulfuric acid, methanesulfonic acid, p-toluenesulfonic acid, nitric acid and trifluoroacetic acid.

In a particular embodiment of the present process, at least one dithiocarboxylic salt is mixed with water before an organic phase is added to this mixture.

Depending on the nature of the reactants, the reaction duration may lie within a wide range, In general, a high conversion is achieved in relatively short times. In general, the reaction duration is in the range from 1 minute to 48 hours, preferably from 30 minutes to 24 hours, and the conversion is determined by analyzing the reaction mixture.

The reaction of the present invention may be carried out within a wide temperature range. Preference is given to this temperature being in the range from minus 10 to 100° C., in particular from 0 to 80° C. and particularly preferably from 15 to 25° C.

In a particular aspect of the present invention, the reaction is carried out under an inert gas atmosphere. Inert gases suitable for this purpose are known to those skilled in the art, and nitrogen or a noble gas, for example, may be used.

After the reaction, the reaction mixture may be purified by known methods. In general, the aqueous is separated from the organic phase, and the reaction product may be purified from the organic phase by known processes, for example chromatography, distillation, extraction and the like. Excess dithiocarboxylic acid or its salts may be removed by extraction with a basic, aqueous solution, for example a sodium hydroxide solution. Olefins or volatile alkyl halides may be removed by evaporation out of the reaction mixture.

However, owing to the high yield, the reaction mixtures may be used as such after removing the aqueous phase, in order to obtain polymers of narrow molecular weight distribution by means of known RAFT techniques.

The invention is further illustrated by examples hereinbelow, although no restriction is intended.

EXAMPLE 1

Cumyl chloride was prepared by shaking 25 g of cumyl alcohol (Aldrich), 0.18 mol) and 150 ml of 37% aqueous hydrochloric acid (Aldrich) in a separating funnel. The cumyl chloride obtained was extracted into 50 ml of heptane, and the heptane solution was admixed with an excess of anhydrous potassium bicarbonate (Aldrich), in order to neutralize the remaining HCl. The heptane solution including cumyl chloride was added to 250 ml of an aqueous sodium dithiobenzoate solution which was prepared according to Mitsukami at al. Macromolecules, 34, No. 7, 2249 (2001) and contained approx. 0.2 moles of sodium dithiobenzoate. A drop of aliquat 330 (Aldrich, tricaprylmethylammonium chloride was added. The biphasic mixture was stirred under nitrogen for 16 hours. After this time, the initially brown-colored aqueous phase became light yellow, and the organic phase above it showed an intense violet coloration. After removing the heptane, 41 g of cumyl dithiobenzoate were obtained, which means a yield of 84% based on the cumyl alcohol.

EXAMPLE 2

300 ml of an aqueous sodium dithiobenzoate solution which was prepared according to Mitsukami et al. Macromolecules, 34, No. 7, 2249 (2001) and contained approximately 0.25 mole of sodium dithiobenzoate, 15.8 g of 1,3-diisopropenylbenzene (Aldrich, 0.1 mol, 0.2 equivalents) and 50 ml of heptane were introduced into a 500 ml separating funnel. Approx. 3 ml of aqueous hydrochloric acid (37%, Aldrich) were repeatedly added thereto. After adding the acid, the mixture was shaken, The brown color of the aqueous layer became light yellow and the color of the organic layer became deep violet. After 16 hours, the organic phase was separated from the aqueous phase. The organic phase was then extracted with 2% aqueous sodium hydroxide solution until the aqueous phase no longer became brown. The organic phase was then washed with three 50 ml portions of water. After removing the heptane, 26.5 g of a deep violet oil were obtained. This oil was purified by chromatography using a silica gel column, and 10.6 g (27%) were obtained.

EXAMPLE 3

100 ml of a 3 M phenylmagnesium bromide solution in diethyl ether were added to 35 g of carbon disulfide in 150 ml of tetrahydrofuran (THF), while maintaining the temperature below 40° C. After one hour, the reaction was terminated by adding 50 ml of water. Ether and THF were removed by a rotary evaporator, after which the mixture obtained was transferred into a 500 ml separating funnel by adding 150 ml of water. 50 ml of heptane and 40 g of α-methylstyrene were added thereto, Concentrated aqueous hydrochloric acid was then added in portions, shaking vigorously each time. The addition of hydrochloric acid was continued until the aqueous layer was virtually colorless. The pH of the aqueous phase fell to a value of less than 7. The organic phase became deep violet, and this color is characteristic of the dithioester. The violet organic phase was separated from the aqueous phase. Volatile materials were removed from the mixture using a rotary evaporator. 93.5 g of a violet oil which contained dithiobenzoic acid were obtained. Dithiobenzoic acid contained in the oil was removed by extraction with 2% sodium hydroxide solution, after which 85 g of cumyl dithiobenzoate were obtained and may be used without further purification in RAFT polymerizations.

The dithiobenzoic acid may again be reacted with α-methylstyrene in a further reaction step, so that virtually 100% of dithiobenzoic acid is reacted.

EXAMPLE 4

32 g of sulfur powder were added to 432 g of a 12% sodium methoxide solution. 63 g of benzoyl chloride were added dropwise to this solution with stirring over 1 hour. The temperature rose to 43° C., and a brown coloration occurred. After all the benzoyl chloride had been added, the reaction mixture was heated to 67° C. for 5 hours, then cooled to 7° C. A precipitate formed and was removed from the reaction mixture by filtration. The precipitate was washed with methanol, after which the methanol was removed with the aid of a rotary evaporator.

The solid obtained was transferred into a 500 ml separating funnel with the aid of 400 ml of water. The aqueous solution was extracted with three 50 ml portions of toluene.

188.2 g of the aqueous solution obtained (containing approx. 0.173 mol of sodium dithiobenzoate) were transferred into a 250 ml separating funnel. 20.5 g of α-methylstyrene and 30 ml of heptane were added thereto. Portions of 37% aqueous hydrochloric acid were added thereto, shaking vigorously after each addition. The hydrochloric acid addition was continued until the aqueous phase was virtually colorless and had a pH of less than 7. The organic phase was extracted using 2% aqueous sodium hydroxide solution. Volatile materials were then removed. 31.5 g of a deep violet oil were obtained.

What is claimed is:

1. A process for preparing a dithioester, comprising:
    reacting a) a benzenedithiocarboxylic acid or b) a benzenedithiocarboxylic salt or c) a mixture of a) and b) represented by formula (I)

(I)

wherein $R_1$ is a group having from 1 to 20 carbon atoms, m is an integer from 1 to 6, and M is a hydrogen atom, an alkali metal ion, an ammonium ion or a group having an alkaline earth metal ion with a (i) vinyl compound of formula (II)

(II)

wherein $R_2$, $R_3$, $R_4$ and $R_5$ are each independently hydrogen or a radical having from 1 to 20 carbon atoms or (ii) an alkyl compound which has a leaving group and is represented by formula (III)

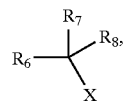

(III)

wherein $R_6$ $R_7$ and $R_8$ are each independently hydrogen or a radical having from 1 to 20 carbon atoms, and X is a leaving group or iii) a mixture of i) and ii) in a biphasic system;
   wherein one phase of said biphasic system comprises water,
   wherein the other phase of said biphasic system is an organic phase; and
   wherein a weight ratio of said phase comprising water to said organic phase is from 95:5 to 5:95.

2. The process as claimed in claim 1, wherein said organic phase comprises an inert organic solvent.

3. The process as claimed in claim 2, wherein said inert organic solvent is an aliphatic hydrocarbon.

4. The process as claimed in claim 3, wherein said aliphatic hydrocarbon is selected from the group consisting of hexane, heptane, octane and nonane.

5. The process as claimed in claim 2, wherein said inert organic solvent is a mineral oil.

6. The process as claimed in claim 1, wherein said dithiocarboxylic salt is dissolved in said phase comprising water.

7. The process as claimed in claim 1, wherein the pH of said phase comprising water is less than or equal to 6.

8. The process as claimed in claim 7, wherein said phase comprising water is admixed with a strong acid.

9. The process as claimed in claim 8, wherein the acid is selected from the group consisting of HCl, HBr, HI; $H_2SO_4$, methanesulfonic acid, p-toluenesulfonic acid, nitric acid and trifluoroacetic acid.

10. The process as claimed in claim 1, wherein a haloalkyl compound or a vinyl compound or a mixture of a haloalkyl compound and a vinyl compound is dissolved in said organic phase.

11. The process as claimed in claim 1, wherein a) said dithiocarboxylic acid or b) said dithiocarboxylic salt or c) said a mixture of a) and b) has at least one free-radical-stabilizing substituent.

12. The process as claimed in claim 11, wherein said free-radical-stabilizing substituent is selected from the group consisting of —CN, —COR and —$CO_2R$,
   wherein R is an alkyl radical, an aryl radical, an aromatic group or a heteroaromatic group.

13. The process as claimed in claim 1, wherein said reaction proceeds in the presence of a phase transfer catalyst.

14. The process as claimed in claim 1, wherein the weight ratio of said phase comprising water to organic phase ranges from 80:20 to 20:80.

15. The process as claimed in claim 1, wherein said reacting is carried out at a temperature of from −10 to 1000° C.

16. The process as claimed in claim 1, wherein said reaction is conducted under a protective gas atmosphere.

17. The process as claimed in claim 1, wherein said alkyl compound which has a leaving group an alkyl halide, an alkyl compound having a pseudohalide group or an alkyl compound having a sulfonate group.

18. The process as claimed in claim 1, wherein said dithiocarboxylic acid or said dithiocarboxylic salt is represented by formula (I)

(I)

wherein
   $R_1$ is a group having from 1 to 20 carbon atoms,
   m is an integer from 1 to 6, and
   M is a hydrogen atom, an alkali metal ion, an ammonium ion or a group having an alkaline earth metal ion.

19. The process as claimed in claim 1, wherein said dithiocarboxylic acid or said dithiocarboxylic salt is reacted with a vinyl compound of formula (II)

(II)

wherein $R_2$, $R_3$, $R_4$ and $R_5$ are each independently hydrogen or a radical having from 1 to 20 carbon atoms.

20. The process as claimed in claim 19, wherein at least one of $R_2$, $R_3$, $R_4$ and $R_5$ is an aromatic group.

21. The process as claimed in claim 1, wherein said dithiocarboxylic acid or said dithiocarboxylic salt is reacted with a compound which has a leaving group and is represented by formula (III)

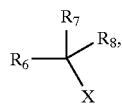
(III)

wherein $R_6$ $R_7$ and $R_8$ are each independently hydrogen or a radical having from 1 to 20 carbon atoms, and X is a leaving group.

22. A process for preparing cumyl dithiobenzoate, comprising:

reacting a) a benzenedithiocarboxylic acid or b) a benzenedithiocarboxylic salt or c) a mixture of a) and b) with i) α-methylstyrene or ii) a cumyl compound which has a leaving group or iii) a mixture of i) and ii) in a biphasic system;

wherein one phase of said biphasic system comprises water;

wherein the other phase of said biphasic system is an organic phase; and wherein a weight ratio of said phase comprising water to said organic phase is from 95:5 to 5:95.

* * * * *

UNITED STATES PATENT AND TRADEMARK OFFICE
CERTIFICATE OF CORRECTION

PATENT NO. : 6,841,695 B2
DATED : January 11, 2005
INVENTOR(S) : Joseph Martin Bollinger et al.

It is certified that error appears in the above-identified patent and that said Letters Patent is hereby corrected as shown below:

Column 10,
Line 29, "from 10 to 1000°" should read -- 10 to 100° --.

Signed and Sealed this

Thirty-first Day of May, 2005

JON W. DUDAS
*Director of the United States Patent and Trademark Office*